United States Patent [19]

Colone

[11] 4,027,675
[45] June 7, 1977

[54] METHOD FOR IMPLANTING HAIR

[76] Inventor: Anthony S. Colone, 8580 Saratoga, Oak Park, Mich. 48237

[22] Filed: Oct. 17, 1975

[21] Appl. No.: 623,403

[52] U.S. Cl. .................................. 128/330; 3/1
[51] Int. Cl.² .................................. A61B 17/00
[58] Field of Search ........................ 128/1 R, 330

[56] References Cited

UNITED STATES PATENTS

| | | | |
|---|---|---|---|
| 3,062,214 | 11/1962 | Maxwell | 128/330 |
| 3,553,737 | 1/1971 | Bauman | 128/330 X |
| 3,608,095 | 9/1971 | Barry | 128/330 X |
| 3,621,837 | 11/1971 | Gindes | 128/330 X |

*Primary Examiner*—Channing L. Pace

*Attorney, Agent, or Firm*—Gifford, Chandler, Sheridan & Sprinkle

[57] ABSTRACT

Hair is implanted in skin by stitching the hair in a manner to form loops which pass through the subcutaneous tissue and to leave a length of hair protruding from each point of entry of the hair into the skin and a length of hair protruding from each exit point of the hair from the skin. A length of hair from one such stitch is tied to a length of hair from a second such stitch. A novel frame comprising a plurality of spaced posts is suggested for holding loops of hair during the stitching. A novel needle has a diameter of about 0.003–0.006 inches and is provided with a hole for threading at its pointed end.

9 Claims, 8 Drawing Figures

METHOD FOR IMPLANTING HAIR

BACKGROUND OF THE INVENTION

A wide variety of means have been suggested for the covering of bald skin with real hair and with synthetic fibers resembling hair. For example, there are toupees, the transplanting of a person's hair from one part of the body to another, the insertion of plugs of hair into skin follicles, the anchoring of "grids" to which additional hair is secured, and the like.

Each of these has had a significant disadvantage—an unnatural appearance of toupees, a rejection by the skin of transplants and of plugs, the difficulty and inconvenience of some of the methods such as transplanting and insertion of plugs, the unaesthetic appearance of a wind-blown "grid".

One method of hair implantation which has appeared, superficially at least, to show promise has been the sewing or stitching of hair or fibers directly into the skin in much the same manner a seamstress sews a thread into a piece of cloth. Such a method can be carried out relatively quickly, economically, with considerably less inconvenience to the recipient of the hair, and with the meeting of aesthetic standards. This method has been tried by inserting a stitch into the skin to form a loop inside the skin while leaving a length of hair protruding from the point of entry of the hair and a length protruding from the exit point. These two lengths have been tied together to form a knot close to the skin. However, this method also results in rejection of substantially all the loops of hair. I am not certain why this rejection occurs, but I believe it results from the fact that an outward pull created by scab formation is in the same plane as the pull created by tying the knot (to be discussed hereinafter in connection with FIG. 1).

There is, therefore, a need for a method of permanently implanting hair which is relatively quick, more economical, more convenient for the recipient, and acceptable aesthetically. The present invention is such a method.

STATEMENT OF THE INVENTION

The present invention is a variation of the above-described stitching method. However, I have found that the rejection of the loop of hair can be successfully avoided if (a) one puts a plurality of such stitches into the subcutaneous layer of the skin each with a length of hair protruding respectively from the inlet point and exit point of the loop and (b) tying a length of hair from one such stitch to a length of hair from a second such stitch to form a knot close to the skin.

Although the stitches can be inserted in the skin in any suitable manner, I have found that a minimal injury to the skin with a maximum flexibility in methods of stitching can be accomplished with a needle having a diameter in the range of about 0.003–0.006 inches and having its eye near the pointed end thereof.

In a preferred embodiment of the invention, a frame provided with posts is positioned against the skin of the hair recipient. As the stitches are made in the skin, threads are looped over posts to position the threads in an orderly array so that they, subsequently, may be easily selected for cutting and tying in the manner contemplated by the invention.

As used herein, the term "hair" means human hair, animal hair, synthetic fibers, or other thread-like material simulating the appearance of hair. The terms "knot" and "tying", as used herein, include not only the familiar interlacement but also the fusion, gluing, or the like, of two hairs or fibers.

Figure 4:
Figure 5:
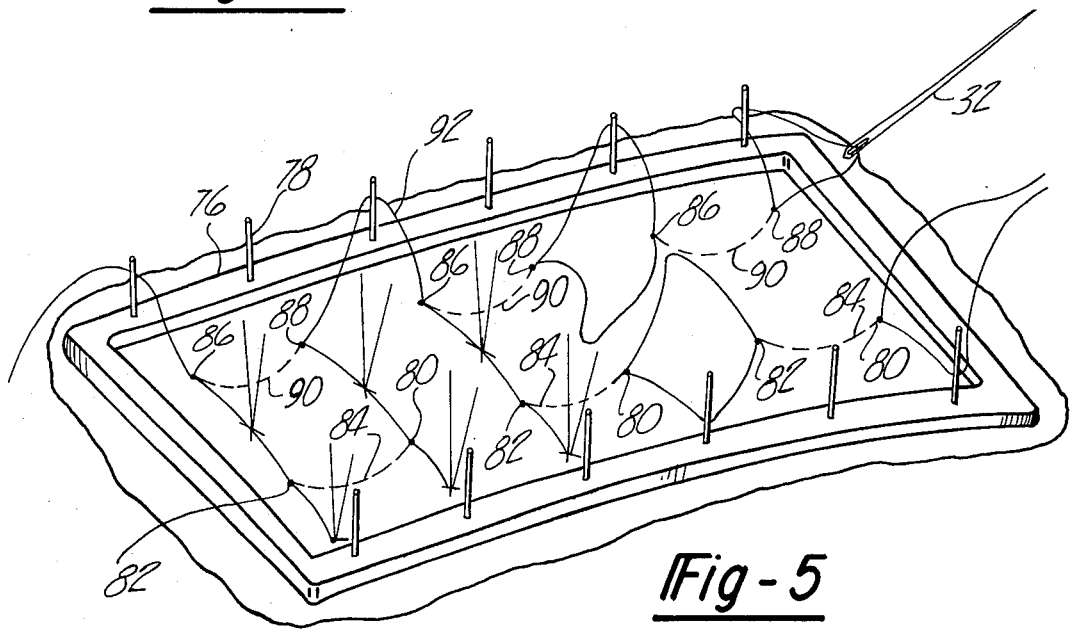
Figure 7:
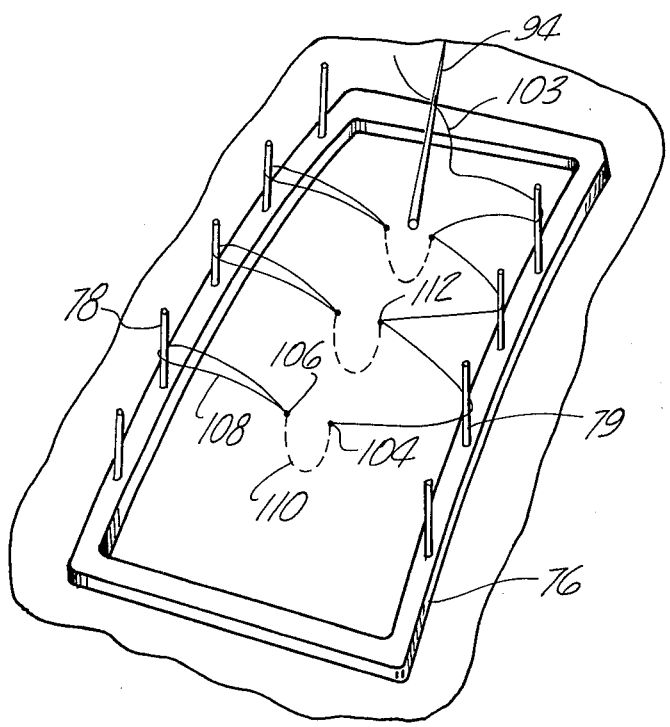
Figure 6:
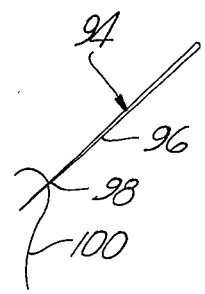

FIG. 4 similarly illustrates another embodiment of the invention;

FIG. 5 similarly illustrates yet another embodiment of the invention;

FIG. 6 illustrates a uniquely valuable form of needle for use in the method of the invention; and FIG. 7 illustrates a method of using the needle of FIG. 6.

Figure 3:
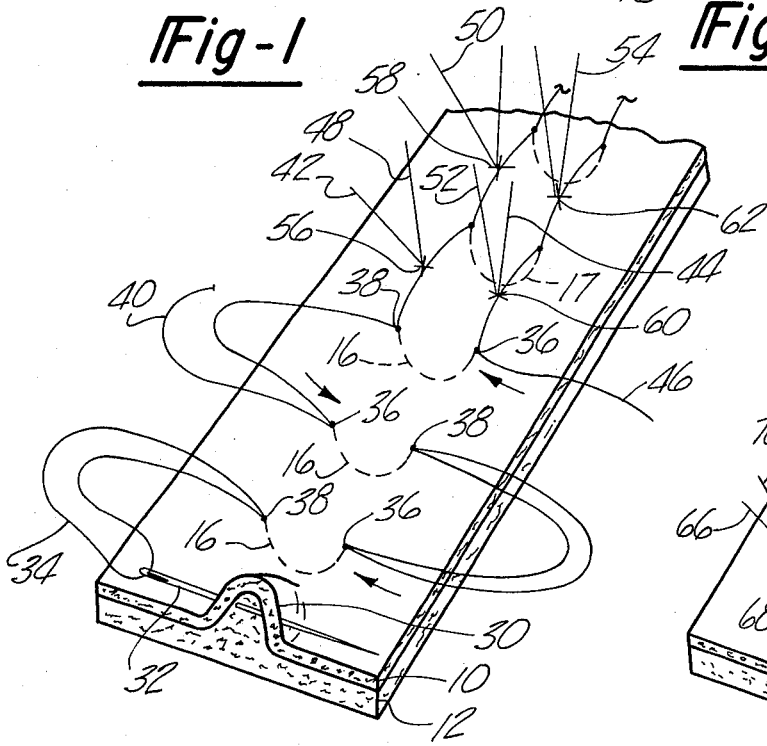
FIG. 3 is a diagrammatic perspective view of skin illustrating an embodiment of the invention.
Figure 8:
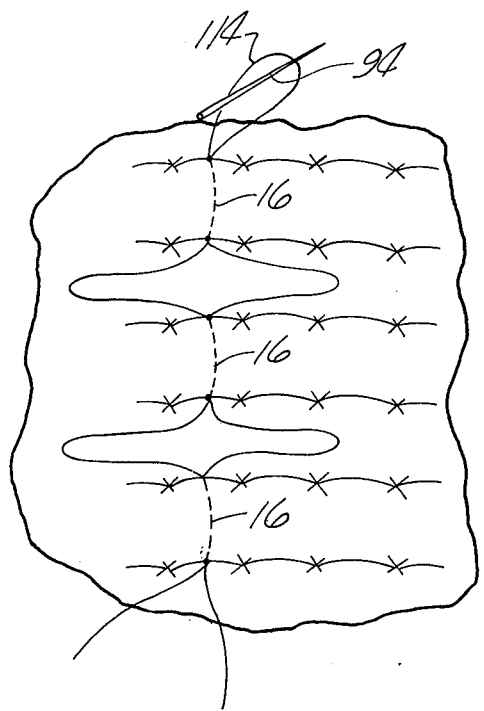

FIG. 8 illustrates the method of FIG. 3 as used where hair is implanted in areas between natural hairs or previously implanted hairs.

Figure 1:
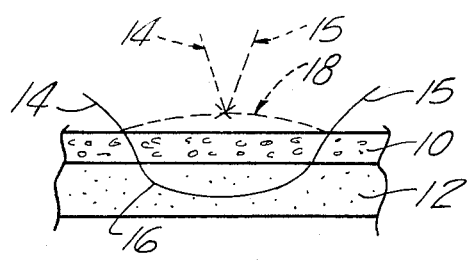
FIG. 1 is a diagrammatic cross section of skin illustrating a method of inserting hair into skin and tying the ends of the hair, which method I have found to be unsatisfactory.

Referring to FIG. 1, a section of skin comprises the combined dermal and epidermal layer 10 and the subcutaneous layer 12. As illustrated, a loop of hair or fiber 14 has been passed through the epidermis and dermal layer into the subcutaneous layer, and then back out through the epidermal and dermal layer to form the loop 16. The phantom line 18 illustrates the bringing together of the two hair ends 14, 15 and the tying of a knot at X (in each instance herein, a knot is symbolized by an X).

Such a tying of a knot X, as illustrated in FIG. 1, together with scab formation in the healing tissue, tends to pull the loop 16 upwardly and out of the subcutaneous layer. This subsequently leads to rejection of the hair. It may be noted that in FIG. 1, the entry point and exit points of loop 16, the loop 16, and the phantom line 18 are all in the same plane. Thus, as the hair ends are pulled together to form the knot X, the resulting force tending to pull the loop 16 upwardly and the upward pull of scab formation are all additive.

Figure 2:
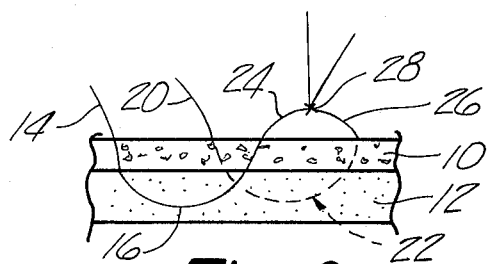
FIG. 2 is similar to FIG. 1 except that the method of the invention is illustrated.

Referring by way of contrast to FIG. 2, two hairs 14 and 20 are shown in perspective forming loops 16 and 22 respectively. As shown an end 24 of loop 16 and an end 26 of hair 20 are tied at knot 28. In this method, the method of the invention, the tying of the knot 28 and the subsequent scab formation do not pull the loops 16 and 22 upwardly out of the subcutaneous layer. It may be noted that, in FIG. 2, the pull resulting from the tying of the knot 28 has a vector perpendicular to the plane of the loop 16.

Referring to FIG. 3, a diagrammatic perspective view of a section of tissue shows a combined epidermal and dermal layer 10, a subcutaneous layer 12, and a raised portion 30, raised as by a pinching of the skin between the fingers (not shown) of an operator. A needle 32 threaded with hair 34 is shown inserted through the skin in a manner to pass a loop of hair through the subcutaneous layer 12 to form a loop 16 similar to loop 16 of FIG. 2.

As indicated in FIG. 3, the various loops 16 have been made by a back and forth stitching with thread 34 as indicated by the arrows, the needle entering the skin at a point 36 and leaving it at a point 38 in the case of each stitch.

Although I prefer to complete all stitching before any cutting or knotting of the hair; FIG. 3, for purposes of explanation, shows some cut and knotted hair and some uncut hair. Thus, threaded hair 34 is continuous from the needle 32 to the pair of cut ends 40 and 42 and the pair of cut ends 44 and 46. Loop 17, by way of example, has been formed by the portion of thread which leads to cut ends 48, 50, 52 and 54; providing one hair end for each of the knots 56, 58, 60 and 62 respectively. Thus, by way of example, knot 56 combines a hair end 42 from a loop 16 and hair end 48 from loop 17 in the manner illustrated in FIG. 2 with respect to hair ends 24 and 26.

FIG. 4 is similar to FIG. 3 except the stitching is done back and forth with a single strand of hair 64 instead of the double strand 34 of FIG. 3. In this case, by way of example, cut end 66 from loop 68 is tied to cut end 70 from loop 72 to form knot 74.

FIG. 5 illustrates a preferred embodiment of the invention. A frame 76 made of plastic, metal, wood or the like, and of any convenient size, shape (preferably generally circular or generally rectangular), and contour (preferably to fit against a generally spherical skin surface) is positioned against a skin area of a person and provided with a plurality of spaced posts, such as post 78. Stitching, in this instance, is done in a line, the needle 32 entering the skin at points 80 and leaving at points 82 in one line to form loops 84; and, in a second line, entering at points 86 and leaving at points 88 to form loops 90. As the stitches are made one of the threads, such as at 92 is looped or hooked over a post 78. This results in an orderly array of the hair and enables the operator to find more easily the hairs he wishes to cut and tie together when the stitching has been completed. I have found that this method speeds up the carrying out of the method to a considerable degree. The latter advantage is important because, at best, hair stitching procedures are long, tedious and therefore expensive.

FIG. 6 shows a preferred form of needle for the method of the invention. The needle 94 comprises a narrow shaft 96, about 0.0003–0.006 inches in diameter, and a hole 98 for thread or hair, such as hair 100.

FIG. 7 shows one manner in which the needle 94 of FIG. 6 can be used in the method of the invention using, by way of example, the form 76 described in connection with FIG. 5.

The needle 94 with hair 103 enters at point 104 and leaves at point 106 at which time a portion of thread 108 is looped over a post, such as post 78. The needle 94 is then withdrawn from entry point 104 to leave the loop 110 in the skin. The hair is then looped over a post such as post 79. The process is then repeated by inserting the needle at point 112.

FIG. 8 illustrates the implanting of hair in areas between the recipient's natural hairs or previously implanted hairs. This step is usually necessary following, for example, the method of FIG. 3 where the space between knots would be, for example, about one-half inch. As illustrated, a line of stitches 16 is made by needle 94 and hair 114 between the previously formed line of stitches. In this manner, a preselected density of hairs can be implanted down to a spacing of, for example, several milimeters.

For purposes of clarity, the knots in the drawings are shown as somewhat loose and spaced from the skin. However, in the practice of the invention, the knots are made sufficiently tight to be close to the skin. It is advantageous to position the knots close to the skin to minimize any tendency to snag the implanted hair with fingernails, brushes, etc.

I claim:

1. A method of implanting hair in living skin which comprises the steps of:
   a. inserting a plurality of lengths of hair into living skin by passing lengths of hair into the skin at an entry point, then into the subcutaneous layer, and then out of the skin at an exit point to form a plurality of stitches and leave at least one length of hair protruding from each said entry and exit point; and
   b. tying knots close to the skin in a plurality of pairs of such hair lengths wherein each such knot joins a length of hair from one such stitch to a length of hair from a second such stitch.

2. The method as defined in claim 1 including the step of forming said stitches as a part of a single continuous piece of hair, and following said stitching, cutting each length at a point intermediate the exit point of one stitch and the entry point of the next succeeding stitch.

3. The method as defined in claim 1 including the step of leaving only one length of hair protruding from each said entry and exit point.

4. The method as defined in claim 1 including the step of leaving two such lengths of hair protruding from each said entry and exit point.

5. The method as defined in claim 2 including the step of forming said stitches in a first substantially straight line and then in a second substantially straight line which is spaced from and substantially parallel to said first line, and wherein cut lengths of hair from said first line are, respectively, tied to cut lengths of hair from said second line.

6. The method as defined in claim 2 including the step of forming each stitch substantially parallel to the preceding stitch.

7. The method as defined in claim 2 including the prior step of forming loops of hair between successive stitches positioned in an orderly array such that individual hair can be more easily identified during the subsequent cutting thereof.

8. The method as defined in claim 1 including the step of threading a needle with said hair and pulling said needle completely through said skin.

9. The method as defined in claim 8, said method further comprising pulling said needle through said skin to a point where said hair has exited, fixing the position of said exited hair, and withdrawing said needle from said entry point.

* * * * *

UNITED STATES PATENT AND TRADEMARK OFFICE
CERTIFICATE OF CORRECTION

PATENT NO. : 4,027,675
DATED : June 7, 1977
INVENTOR(S) : Anthony S. Colone

It is certified that error appears in the above-identified patent and that said Letters Patent are hereby corrected as shown below:

Col. 3, line 2, delete "semi-colon" (;), insert --comma-- (,);
line 42, delete "0.0003", insert --0.003--.
Col. 4, line 50, delete "hair", insert -- hairs --.

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademarks*